United States Patent
Bueler et al.

(10) Patent No.: US 10,729,585 B2
(45) Date of Patent: Aug. 4, 2020

(54) COMPUTER PROGRAM FOR OPHTHALMOLOGICAL SURGERY

(75) Inventors: Michael Bueler, Zurich (CH); Michael Mrochen, Nanikon (CH)

(73) Assignee: Alcon Inc., Fribourg (CH)

( * ) Notice: Subject to any disclaimer, the term of this patent is extended or adjusted under 35 U.S.C. 154(b) by 2000 days.

(21) Appl. No.: 11/489,251

(22) Filed: Jul. 19, 2006

(65) Prior Publication Data

US 2008/0033408 A1 Feb. 7, 2008

(51) Int. Cl.
*A61F 9/008* (2006.01)
*A61B 34/10* (2016.01)

(52) U.S. Cl.
CPC .......... *A61F 9/008* (2013.01); *A61F 9/00806* (2013.01); *A61F 9/00825* (2013.01); *A61B 34/10* (2016.02); *A61F 2009/0087* (2013.01); *A61F 2009/00872* (2013.01)

(58) Field of Classification Search
CPC ......... A61B 19/50; A61B 34/10; A61F 9/008; A61F 9/00806; A61F 9/00825; A61F 2019/0087; A61F 2019/00872; A61F 2009/00872; A61F 2009/0087
USPC ............................................ 606/4–6, 10–123
See application file for complete search history.

(56) References Cited

U.S. PATENT DOCUMENTS 4,669,466 A * 6/1987 L'Esperance ...................... 606/3
5,460,627 A * 10/1995 O'Donnell, Jr. ................... 606/4
5,891,131 A * 4/1999 Rajan .................. A61F 9/00804 606/5

(Continued)

FOREIGN PATENT DOCUMENTS

DE 100 14 480 9/2001 ............. A61B 3/107
EP 1 327 948 A2 7/2003 ............... A61B 3/10

(Continued)

OTHER PUBLICATIONS

E. Spörl et al., "Untersuchungen zur Verfestigung der Hornhaut am Kaninchen", Ophthalmologe, 97:203-206 with English Abstract & Unedited Machine Translation, 10 pages, 2000.

(Continued)

*Primary Examiner* — Catherine M Voorhees
(74) *Attorney, Agent, or Firm* — Baker Botts L.L.P.

(57) ABSTRACT

A Computer program for determining a working profile for controlling a radiation system in refractive eye surgery, said program comprising:

a user interface for input of data by a user; a data receiving interface for receiving measured data regarding the eye to be corrected; a working profile generator for generating a working profile on the basis of the input data and measured data; a generator for generating control data for controlling electromagnetic radiation; a simulator for simulating a treatment result on the basis of said control data for controlling the electromagnetic radiation and the effect of said radiation on eye tissue; a judgment stage for judging said treatment results by applying pre-given criteria; an iteration loop for generating iteratively, in case of a negative judgment, another amended profile on the basis of other data or for generating iteratively other control data for controlling the electromagnetic radiation; and a transfer means for transferring control data to a control of the radiation system in case of a positive judgment in the judgment stage.

15 Claims, 10 Drawing Sheets

(56) References Cited

U.S. PATENT DOCUMENTS

| | | | |
|---|---|---|---|
| 6,673,062 B2* | 1/2004 | Yee et al. .................... 606/5 |
| 6,749,632 B2* | 6/2004 | Sandstedt ............ A61B 3/1015 |
| | | | 623/6.22 |
| 6,887,231 B2* | 5/2005 | Mrochen ............. A61F 9/00806 |
| | | | 606/10 |
| 7,252,380 B2* | 8/2007 | Koest .................... A61B 3/1005 |
| | | | 351/205 |
| 2003/0105457 A1* | 6/2003 | Mrochen ............. A61F 9/00806 |
| | | | 606/5 |
| 2003/0225399 A1 | 12/2003 | Chernyak et al. ................. 606/5 |
| 2005/0007551 A1* | 1/2005 | Wakil ..................... A61B 3/107 |
| | | | 351/205 |
| 2013/0190736 A1* | 7/2013 | Fabrikant ............ A61F 9/00806 |
| | | | 606/5 |

FOREIGN PATENT DOCUMENTS

| | | | | |
|---|---|---|---|---|
| WO | 2001/085075 A1 | 11/2001 | ............. A61F 9/013 |
| WO | 2002/007660 A2 | 1/2002 | ............... A61F 9/01 |
| WO | 2005/074848 | 8/2005 | ............. A61F 9/008 |

OTHER PUBLICATIONS

Grigoropoulos, Costas P., "Laser Ablation and Desorption—Lasers, Optics, and Thermal Considerations in Ablation Experiments," Experimental Methods in the Physical Sciences, vol. 30, pp. 173-174, 1998.

G. Wollensak et al., "Riboflavin/ultraviolet-a-induced collagen crosslinking for the treatment of karatoconus", Am J Ophthalmol., 135(5):620-627, May 2003.

G. Wallensak et al., "Stress-strain measurements of human and porcine corneas after riboflavin-ultraviolet-A-induced cross-linking", J. Cataract. Refract. Surg., 29(9):1780-1785, Sep. 2003.

E. Spoerl et al., "Untersuchungen zur Verfestigung der Hornhaut am Kaninchen", Ophthalmologe, 97(3):203-206, 2000.

F. Manns et al., "Ablation profiles for wavefront-guided correction of myopia and primary spherical aberration", J. Cataract. Refract. Surg., 28(5):766-774, May 2002.

D. Huang et al., "Mathematical model of corneal surface smoothing after laser refractive surgery", Am. J. Ophthalmol., 135(3):267-278, Mar. 2003.

* cited by examiner

COMPUTER PROGRAM FOR OPHTHALMOLOGICAL SURGERY

FIELD OF THE INVENTION

The present invention is concerned with a computer program for ophthalmological surgery, in particular, the present invention is concerned with a computer program for determining a working profile for refractive eye surgery and for control of a laser system the emitted radiation of which effects a surgical intervention. The invention is also concerned with a method for generating a control program which is used to perform ophthalmological surgery by means of laser radiation or other electromagnetic radiation. Accordingly, the invention is also concerned with a computer system and a device for ophthalmological surgery using a computer program in accordance with the present invention and using, in particular, a control program that is generated in accordance with the present invention.

BACKGROUND INFORMATION

It is prior art to perform surgical operations for correction of ametropia or other therapeutical treatments (e.g. cuts for ceratoplastics) by means of laser radiation or other radiation interacting with parts of the eye in order to change the optical properties of the eye in a selected manner. Most prominent example of the interaction between laser radiation and the eye is the re-shaping of the cornea by ablation (removal of tissue). The present state of the art typically uses the well-known LASIK technique. The present invention is, in particular, concerned with LASIK technique, however, the invention is generally concerned with ophthalmological surgery with radiation, are in particular laser radiation. Sources for laser radiation, modified in particular UV-sources (e.g. excimer-lasers), IR-sources (e.g. erbium:YAG laser) as well as ultrashort laser pulses (e.g. titan:saphire, Cr:LiSAF, Nd:YLF).

It is also prior art to implant an artificial eye lens (intraocular lens) into the eye by means of a surgical action in order to correct the eye optically. Certain intraocular lens types can be modified after implantation by action of light (e.g. UV-radiation) in order to change the form or the optical effect of the lens. It is also known that certain materials exposed to high light intensities (e.g. ultra-short laser pulses) change its refractive properties, i.e. its index of refraction.

In the prior art the changes of form or certain optical structures of the eye, e.g. the cornea, are calculated on the basis of clinical data (e.g. data regarding ametropia) and corresponding theoretical models (eye models). From the difference between a preoperative form and a theoretical postoperative form of the eye structure to be changed, the so-called treatment profiles or working profiles can be derived and according to such profiles the laser radiation is controlled in space and time. This is all well-known to a person skilled in the art. For example, a preoperative cornea curvature minus a wanted postoperative cornea curvature results in a volume of cornea tissue that is ablated in order to obtain a change in the form of the cornea such that the wanted optical change of the optical system of the entire eye is achieved.

If pulsed laser radiation is used in the so-called spot-scanning-method, i.e. single laser pulses are focused such that its diameters are small as compared to the extension of the cornea and are successively scanned over the cornea, the prior art teaches to generate a complete control program for laser pulses in space and time on the basis of certain assumptions regarding the tissue removal effected by each laser pulse. A list of x, y, z-positions of the laser pulses is derived and, according to that list, the ablation of the cornea surface or the interaction between the laser radiation and the eye tissue is performed. The latter is, at present, mostly performed by ultra-short laser pulses.

It is also known in the prior art, to consider certain factors which have an effect on the result of the surgical action when generating the list of single laser pulses. Such influential factors can be the healing process, biomechanical changes by the intervention itself, smoothing effects in the tissue as well as a tear film.

Such factors to be reckoned on are typically determined empirically on the basis of clinical data and by means of certain evaluation functions, e.g. the point-spread function, modulation transfer function etc. The observation and quantitative calculation of such factors is known to a person skilled in the art.

In the prior art the positions of the individual laser pulses are calculated with reference to a reference axis to be determined. Very often the "line of sight" is selected as the reference axis. This reference axis is then used to control the laser systems. As is known, suitable means for forming and guiding the beam are used in order to shape the individual laser pulses and position them in space. The positioning is performed in three dimensions wherein the x, y, z-coordinates are typically used such that the x, y-plane is perpendicular to the line of sight, whereas the z-axis is in that line. The z-coordinate, therefore, is related to the focusing of the laser beam.

According to EP 1 327 948 A2 a list of laser pulses for ablation is generated by determining for a patient on the basis of aberration measurements a correction list. Thereafter, a databank is used in which surgical results obtained with other patients under similar conditions are stored. On the basis of such data a correction of the initial list is performed. This results in the eventually used ablation profile.

US 2003/0225399 A1 teaches to simulate an alignment error. An iteration algorithm is used to measure an actually ablated surface. That measurement serves in the iteration loops as a comparative value.

WO 02/07660 A2 describes a method for determining an ablation profile under consideration of several parameters, however, there is no combination of simulating, judging and generating iteratively on the basis of negative judgments.

It is known in the prior art (WO 01/85075A1) to take account of reflection losses caused by different angles of incidence upon the cornea when determining an ablation profile. This prior art also teaches to take account of the effect on the fluence caused by different angles of incidence between the radiation and the cornea surface. It is also known to consider the postoperative healing process.

All these known techniques can be improved as they are regularly not specific with respect to the individual patient but rather are based on average values of postoperative clinical results of a large number of patients.

It is known in the prior art to perform refractive surgery wavefront-guided. This results in a remarkable improvement of the results, also at ametropia at higher orders. Nevertheless, such prior art can be improved as the calculation of the ablation profile is based on assumptions and simplifications which limit the precision of the laser interaction.

Prior art according to DE 100 14 480 (Hohla et al.) is based on the observation that a wavefront measurement provides information about the eye, in particular the cornea, in a range within the pupil opening only and that, furthermore, a topography measurement measures also areas of the cornea outside the pupil opening. Accordingly, Hohla combines both measurements. Also a simulation is described how the calculated theoretical ablation profile is subtracted from the preoperative topography in order to obtain the postoperative (wanted) cornea shape. This calculated cornea shape is presented to the doctor on a screen. The doctor shall examine the remaining thickness of the cornea and then decide whether or not the treatment is performed. The simulation has the only purpose to provide a presentation to the doctor as a support to make a decision.

SUMMARY OF THE INVENTION

The present invention aims at providing computer programs and methods for generating such computer programs allowing ophthalmological treatments with improved results.

To this end the invention provides a computer program for determining a working profile in connection with refractive eye surgery and for controlling a radiation system, said program comprising:
- a user interface for input of data by a user,
- a data receiving interface for receiving measured data regarding the eye to be treated,
- a profile change generator for generating an amended profile on the basis of the input data and the measured data,
- a generator for generating control data for controlling electromagnetic radiation,
- a simulator for simulating a treatment result on the basis of said control data for controlling electromagnetic radiation and on the basis of the effect of that radiation upon eye tissue,
- a judgment stage for judging said treatment result by applying pre-given criteria,
- an iteration loop for, in case of a negative judgment, generating iteratively another amended profile on the basis of other data or for generating iteratively other control data for controlling the electromagnetic radiation; and
- a transfer circuit for transfer of control data to a control device controlling the radiation system in case of a positive judgment in the judgment stage.

The afore-mentioned profile is preferably an ablation profile in the above-defined sense, namely a well-defined volume of tissue to be ablated from a cornea.

The afore-mentioned user interface and the data receiving interface can be separate program modules or implemented by one and the same program module.

The afore-mentioned judgment stage is implemented preferably as a fully automatical program module for judging said treatment results on the basis of pre-given judgment criteria. It is, however, also possible to provide in this judgment stage for judgments by a user, in particular on the basis of criteria output by the computer program and presented to the user on a screen.

Different from the above-cited prior art DE 100 14 480 (Hohla) the simulation of the ablation in accordance with the present invention is part of the optimization process to obtain the eventually used ablation profile. In other words, the present invention does not simply subtract the theoretically obtained ablation profile for the purpose of presenting it on a screen (as the cited prior art) but rather the present invention simulates the ablation of individual laser shots taking into account different estimated physical and biological effects aiming at a final result in which erroneous ablations are avoided by compensation beforehand in said ablation profile.

The present invention also teaches a method for generating a control program for performing ophthalmological surgery by means of laser radiation, said method comprising the following steps:
- (a) generating an individualized eye model using data of the individual patient, in particular the initial shape of the cornea,
- (b) determining a reference cornea shape to be achieved by means of iterative three-dimensional ray tracing from the retina using said eye model,
- (c) determining the difference between the reference cornea shape and the initial shape to obtain an initial ablation profile,
- (d) deriving control data for controlling the laser radiation, including positional data regarding the positions of the interaction between the laser radiation and the cornea,
- (e) simulating the interaction between laser radiation controlled in accordance with said control data and the cornea on the basis of said individualized eye model in order to obtain, by performing said ablation profile, a simulated cornea shape,
- (f) comparing said simulated cornea shape with the reference cornea shape by applying pre-given criteria to determine whether or not a difference between the simulated cornea shape and the reference shape is within a pregiven tolerance, and
- (g) iteratively repeating steps (d) to (f) with amended control data until said comparison reveals a difference within said tolerance.

This method for producing a control program can also be applied to an ophthalmological intervention at an eye lens and, in that case, is characterized by the following steps:
- (a) generating an individualized eye model using patient-related data, in particular the initial shape of the eye lens, including its posterior and/or anterior surface,
- (b) determining a reference lens form and its anterior and/or posterior surfaces to be achieved by means of iterative three-dimensional ray tracing from the retina using said eye model,
- (c) determining the difference between the reference lens form and the initial form to obtain an initial working profile,
- (d) deriving control data for controlling the laser radiation, including position data regarding the positions of interaction between the laser radiation and the eye lens,
- (e) simulating the interaction of laser radiation controlled in accordance with the control data and the eye lens on the basis of said individualized eye model, in order to obtain, by processing the initial working profile, a simulated eye lens form,
- (f) comparing the simulated eye lens form with the reference lens form by applying pre-given criteria in order to determine whether or not a difference between the simulated eye lens form and the reference lens form is within a pre-given tolerance, and
- (g) repeating iteratively the steps (d) to (f) with amended control data until said comparison reveals a difference within said tolerance.

The afore-described method for generating a control program to control ophthalmologic surgery at an eye lens can also be used to generate a control program for surgery at an artificial eye lens.

According to a preferred embodiment the user interface of the afore-described computer programs is adapted to receive at least one, preferably a plurality and, more preferably, all of the following data:

Demographic data; clinical data; measured wavefront aberrations; depths of sharpness of the postoperative eye; difference optical zones of the cornea or the eye lens; biometrical dimensions of the eye, e.g. length of the eye, cornea shape; biophysical properties of the eye, like water content of tissue; measuring conditions during diagnostics, e.g. centering relative to a certain reference axis; optical properties of the eye, like pupil diameter or index of refraction; visus value to be achieved; clinical status of the patient; user (doctor).

Furthermore, in accordance with a preferred embodiment of the computer program it is provided that said data receiving interface receives at least one, preferably a plurality and most preferably all of the following measured data:

Energy data regarding the laser radiation; environmental conditions like humidity and/or room temperature; biometrical data regarding the eye including length of eye, shape of cornea; biophysical data regarding the eye, including the water content of the tissue; optical parameters of the eye, including the actual pupil diameter, index of refraction etc.; measuring conditions during diagnostics, including centering with regard to a pre-given reference axis; demographical data regarding the patient; clinical status of patient; data regarding the user (doctor).

The present invention can also be used in the field of UV-cross-linking of the cornea. Most recently methods have been developed for stabilizing the cornea (see PCT/EP2005/001083 "Ophthalmological apparatus"). It was found recently that, depending on the radiation amount (energy rate, dose rate) the cornea is changed regarding it's refractive power. Therefore, the computer program and methods according the present invention can be used to determine a light radiation and light distribution in order to achieve an exact optical correction of the cornea by UV-cross-linking. See, in this regard, the following publications: G. Wollensak, E. Spoerl, T. Seiler in AMERICAN JOURNAL OF OPHTHALMOLOGY, MAI 2003, S. 620; and G. Wollensak, E. Spoerl, T. Seiler in J. Cataract Refract Surgery vol. 29, September 2003, p. 1780; and E. Spoerl, 3. Schreiber, K. Hellmund, T. Seiler, P. Knuschke, in DER OPHTHALMOLOGE, 3; 2000 p. 203.

With the method according to the present invention errors are minimized when calculating a theoretical ablation profile and possible deviations from an ideal ablation profile during real ablation are compensated beforehand. With the method according to the present invention, the wavefront is measured and processed (not just topographical data alone).

BRIEF DESCRIPTION OF THE DRAWINGS

In the following examples of the invention are described with reference to the figures. The figures show.

DETAILED DESCRIPTION

Figure 1:
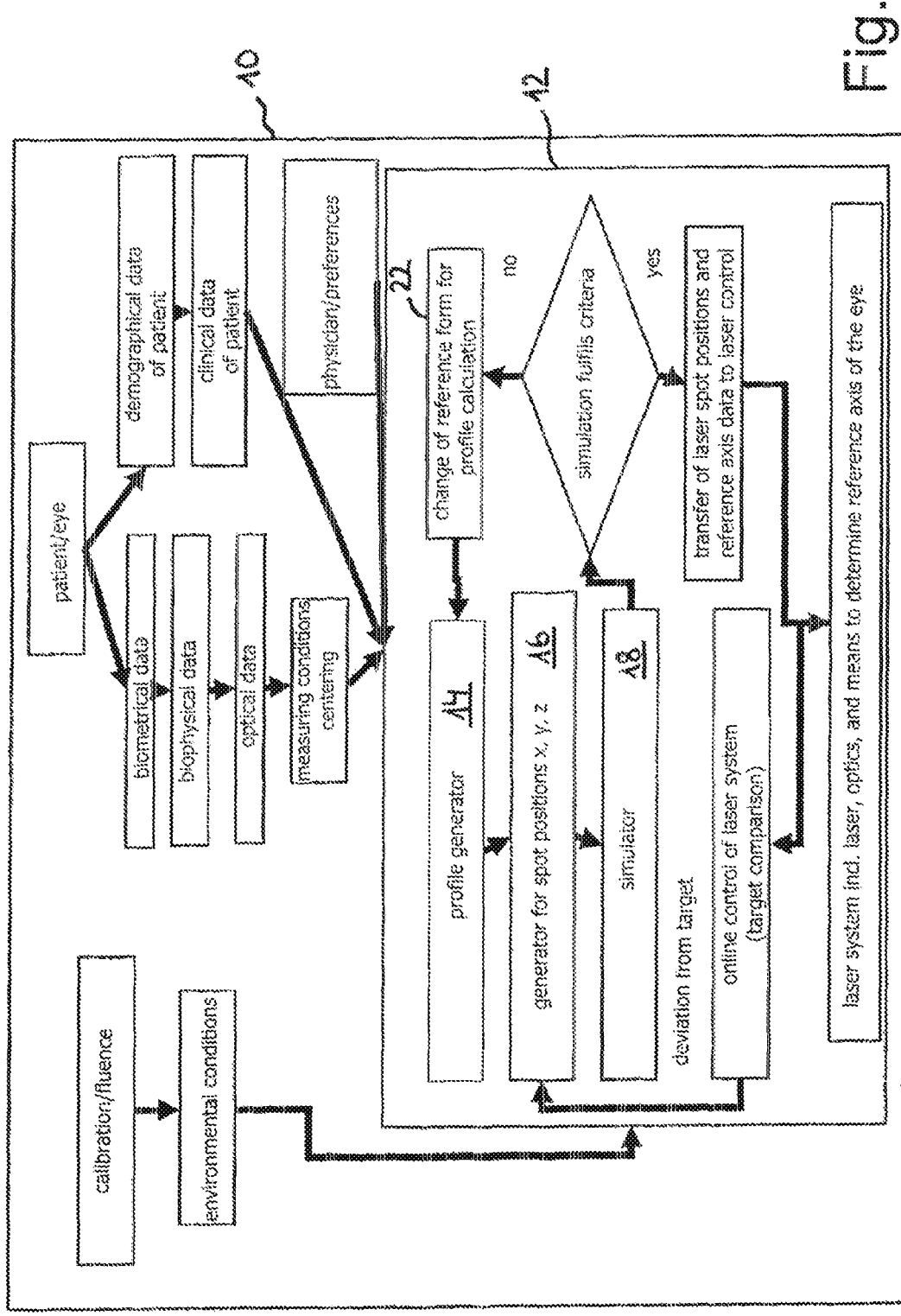
FIG. 1 an aggregate system including an ophthalmological laser system, computer control, measuring, and data acquisition.

FIG. 1 shows a schematic block diagram of a laser system including a computer control and, furthermore, the measuring data and conditions observed when controlling the laser system. Block 10 includes an aggregate system comprising the aforementioned components. Block 12 includes the laser system for eye surgery and in particular the computer control of the laser beam. The block 10, including the aggregate system, contains also data related to the patient and its eye.

The aggregate system 10 comprises, as indicated on top of the block 12 (describing the laser system and its control) data acquisition blocks which are, as such, known to a person skilled in the art. First, data related to the patient and its eye are collected, namely biometrical values, biophysical values, optical values, and measuring data regarding centering. Furthermore, with regard to the patient and its eye, the following data are acquired: Demographical data of the patient (age, constitution etc.), clinical status of patient.

All these data related to the patient and his/her eye are input into the computer control of the laser system 12, as indicated in FIG. 1. In addition, data regarding the physician can be entered into the computer, in particular his favorite treatment conditions, like a minimum wavefront aberration etc.

Furthermore, as indicated in aggregate system block 12, on the left hand side, data regarding calibration and fluence of the laser beam are entered into the computer control of system 12, as well as data regarding environmental conditions, like humidity and temperature.

In the following, the afore-mentioned biometrical data are further explained. The term "biometrical data" includes e.g. the individual eye length of the patient and the shape of the cornea. The prior art typically uses only a statistical average value of the eye length when setting up and eye model. This can result in errors when processing the wavefront aberration as the image locations at the retina depend from the eye length. In particular, the cornea topography is a biometrical data.

Other factors based on the individual eye of the patient are the "biophysical data" like the water content of the tissue which has an affect on the interaction of the laser beam with the tissue. The water content can change during surgery. Therefore, a measurement before surgery and measurements during surgery (on-line) are included.

The term "optical values" includes the pupil diameter of the eye and the index of refraction as well as wavefront errors measured with the patient's eye.

Furthermore, as indicated by the block "measuring conditions, centering" in FIG. 1, the computer receives data regarding the measuring conditions during diagnostics, e.g. conditions during the measurement of the cornea topography or the wavefront aberration. During such measurements a certain reference axis must be used, e.g. the line-of-sight. Such centering of all data must be maintained during the entire procedure.

The block "demographical data of patient" refers to conditions caused by the individual patient, e.g. demographical data (age) and clinical data, e.g. an estimate of the healing conditions of the individual patient depending on the constitution of the patient. Another influential factor can be the treating physician who prefers certain treatment goals and surgical techniques.

Further conditions input via the interface into the computer can be: an intended minimum wavefront error (when using the known measurement of wavefrontaberration), a minimum depth of sight for the postoperative eye, in particular when correcting myopia, or also a definition of different optical zones of the cornea or the eye lens.

All these data are input via the interface (indicated in FIG. 1 by the arrows) into the computer system. That computer system is adapted to calculate a profile for refractive eye surgery and to control a laser system including beam scanning means etc. in correspondence with the generated profile. That system is included in block 12 of FIG. 1 and described in more detail in FIG. 2.

Figure 2:
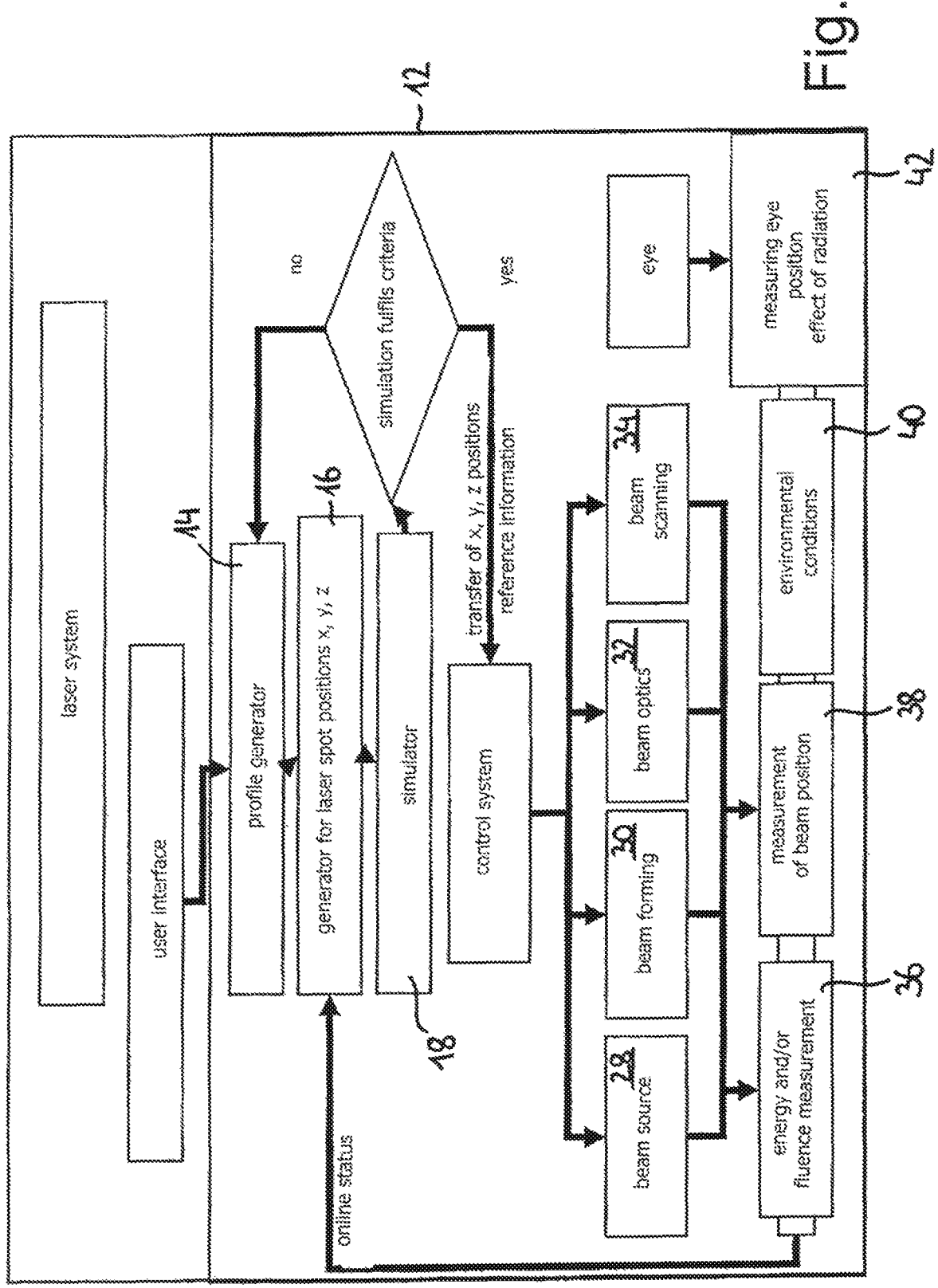
FIG. 2 a schematic block diagram of a computer control according to FIG. 1 with further details.

According to FIGS. 1 and 2 the laser system comprises a treatment profile generator 14. This generator generates, on the basis of the afore-mentioned input data and measuring data, a profile representing the initial goal of the treatment, e.g. an ablation profile for changing the form of the cornea.

Furthermore, the program comprises a generator for generating control data on the basis of the afore-mentioned profile in order to control laser radiation. All this is theoretical calculation only, the actual control of a laser is performed later (see below). This generator calculates, in particular, the x, y, z-positions of the pulsed laser radiation, i.e. the above-described list of sequential laser pulses as a sequence in space and time.

Furthermore, the program comprises a simulator 18 for simulating a treatment result on the basis of the calculated control data and using said profile. The computer, therefore, simulates a treatment without that the treatment is actually performed.

During this simulation, preferably, some or all above stated influential factors and conditions, based e.g. on empirical data, can be used and assumptions are input into the program describing the typical effects of such data.

This yields a theoretical treatment result which is input into a judgment stage. The judgment stage determines whether or not the simulated treatments fulfils certain pre-given judgment criteria, i.e. criteria as to whether or not the optimum treatment result is achieved sufficiently close. This judgment stage is part of an iteration loop going back to the profile generator 14 as indicated in FIGS. 1 and 2. This iteration process observes that the different factors and conditions to be observed (as explained above) can have very complex interrelations (the can "interact" with each other). For example, the laser can reduce the thickness of the cornea such that the inner pressure of the eye changes the shape of the cornea, i.e. the curvature of the cornea can be changed by the pressure. Such effects can be taken care of in the iterative process by decreasing in a second calculation loop the ablation in order to compensate for a bowing due to pressure.

If, eventually, the judgment stage judges that the result obtained theoretically by performing several iteration loops is sufficiently correct within certain tolerance criteria, the iterative process can be terminated and the control data (profile) generated can be input into the control system controlling the laser. Such control-programs to control the laser beam acting upon the eye including x, y, z-positions of the laser pulses and other control data are known as such to a person skilled in the art.

Thereafter, the actual refractive surgery is performed. According to FIG. 2, the laser control controls the light source 28, the laser beam shaping means 30, the laser scanning means 32 and the beam positioning means 34 (e.g. focusing).

FIG. 2 also shows a refinement of the system including means 36 for measuring energy and/or fluence of the laser, means 38 for measuring a beam position, means 40 for measuring environmental conditions (temperature, humidity), and means 42 for measuring the position of the eye (eye-tracker). All these measured data can be input into the generator 16 and the input data can be used to optimize the calculated profile.

Figure 3:
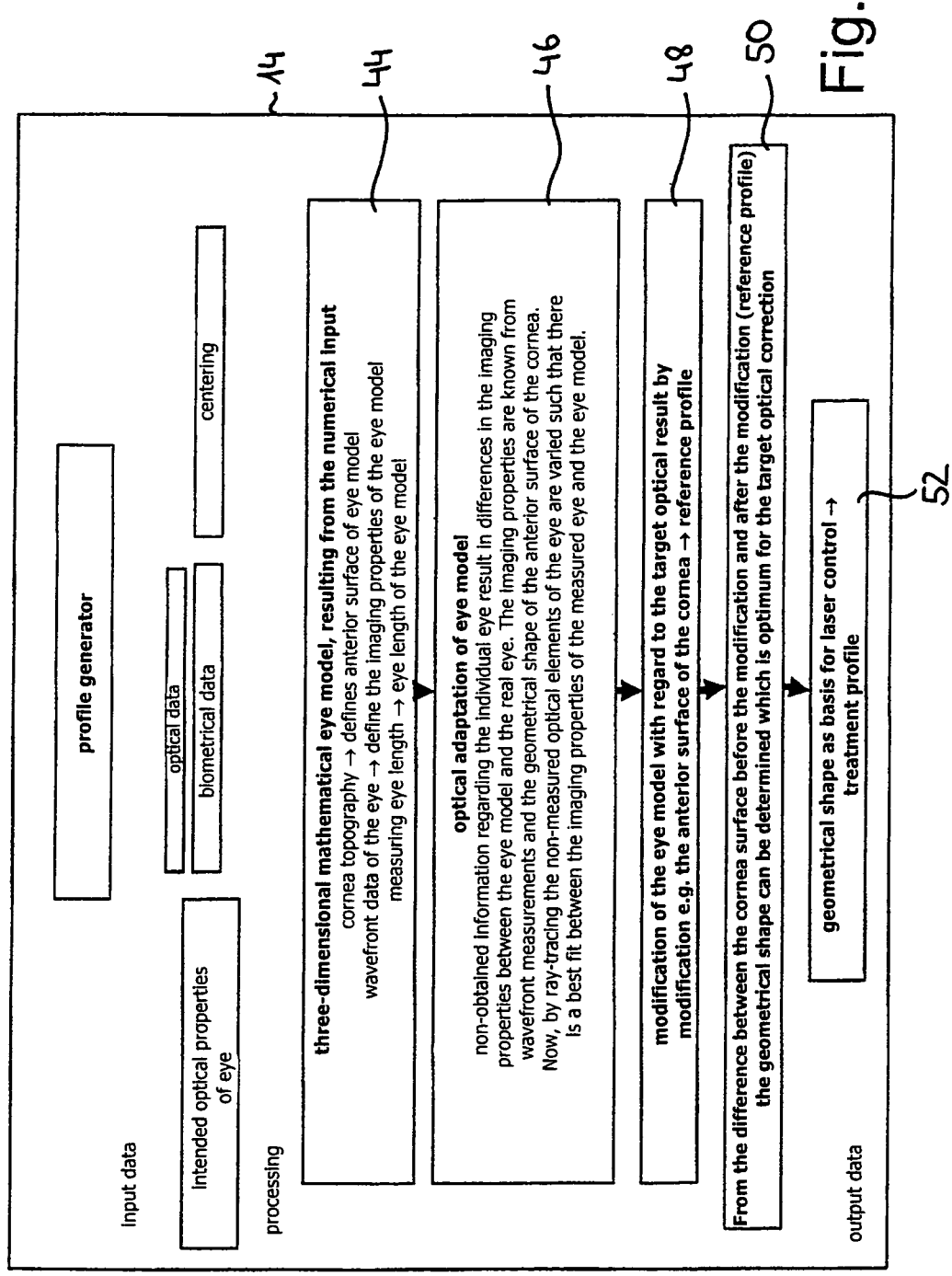
FIGS. 3 to 6 schematic block diagrams of different calculation modules for use with a system according to FIGS. 1 and 2.
Figure 4:
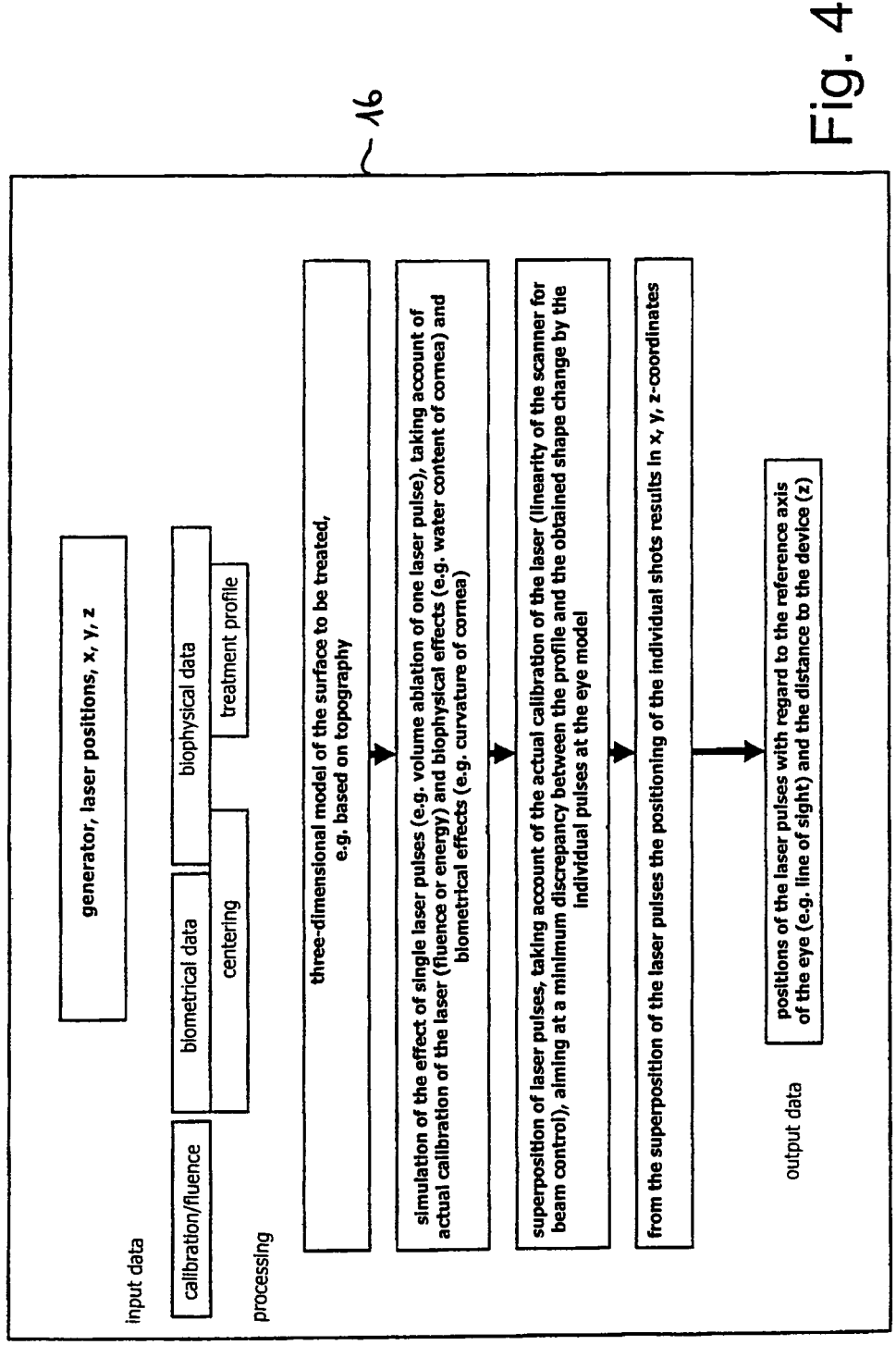
Figure 5:
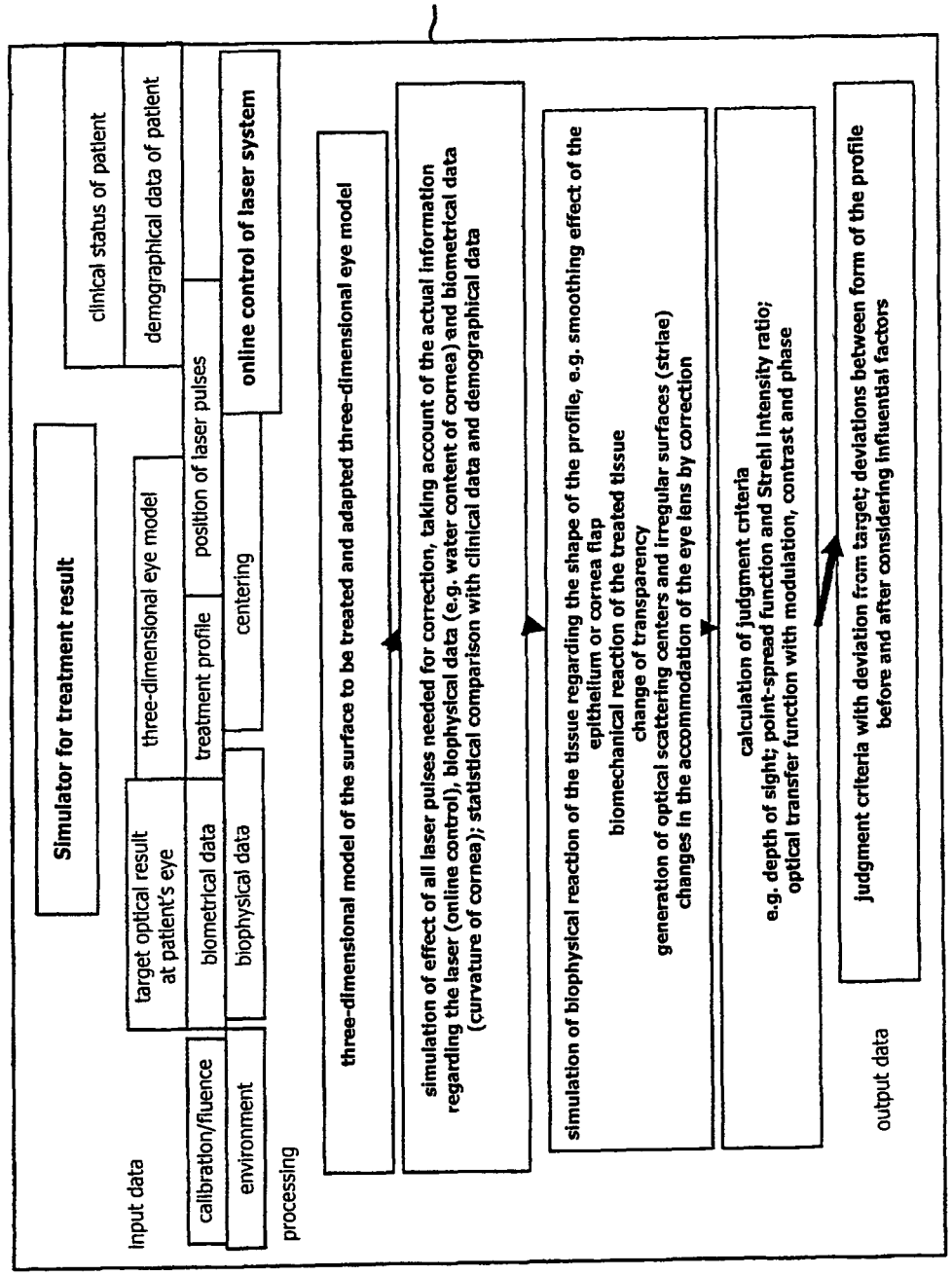

FIGS. 3 to 5 describe in detail the different calculation modules with regard to the input data and output data.

FIG. 3 describes the generator for the profile, e.g. the ablation profile if LASIK is performed. In the different blocks shown in FIG. 3, the input data are indicated (on top of FIG. 1) and the processing is sketched in the other blocks shown in FIG. 3.

A first input data are the target optical results regarding the patient's eye. Further input data are the above-described optical values, biometrical values and measuring conditions, in particular centering.

These data are processed in accordance with the blocks shown in FIG. 13 under the headline "processing".

The first block 44 describes the calculation of the three-dimensional eye model which results from the numerical input, as described above, via the interfaces.

The next block 46 describes a special optical adaptation of the eye model. Most essential data are the imaging properties of the eye based on wavefront measurements and the geometrical shape of the anterior surface of the cornea. Because of incomplete information regarding the individual eye of the patient, however, such an eye model is also incomplete and there are deviations between the imaging properties of the eye model and the real eye. For improving the eye model, therefore, ray-tracing from the retina is performed with the eye model and the optical elements (of the eye) are varied such that there is a best possible agreement between the imaging properties of the real eye and of the eye model. This results in an optimum eye model. The other blocks 48, 50 and 52 show how data are obtained for laser control.

FIG. 4 shows further details of the generator for generating laser control data, in particular positions of the laser spot on the basis of x, y, z-coordinates. FIG. 4 shows the input data and the processing steps.

FIG. 5 shows details of the simulator for simulating a treatment result. On top of FIG. 5, the input data are presented and, under the headline "processing" the steps are indicated, whereas the last block in FIG. 5, at the bottom, presents the output data. FIG. 5 discloses the specific consideration of the above-indicated treatment conditions and influential (effective) factors. The single processing steps are presented and the resulting output data.

Figure 6:
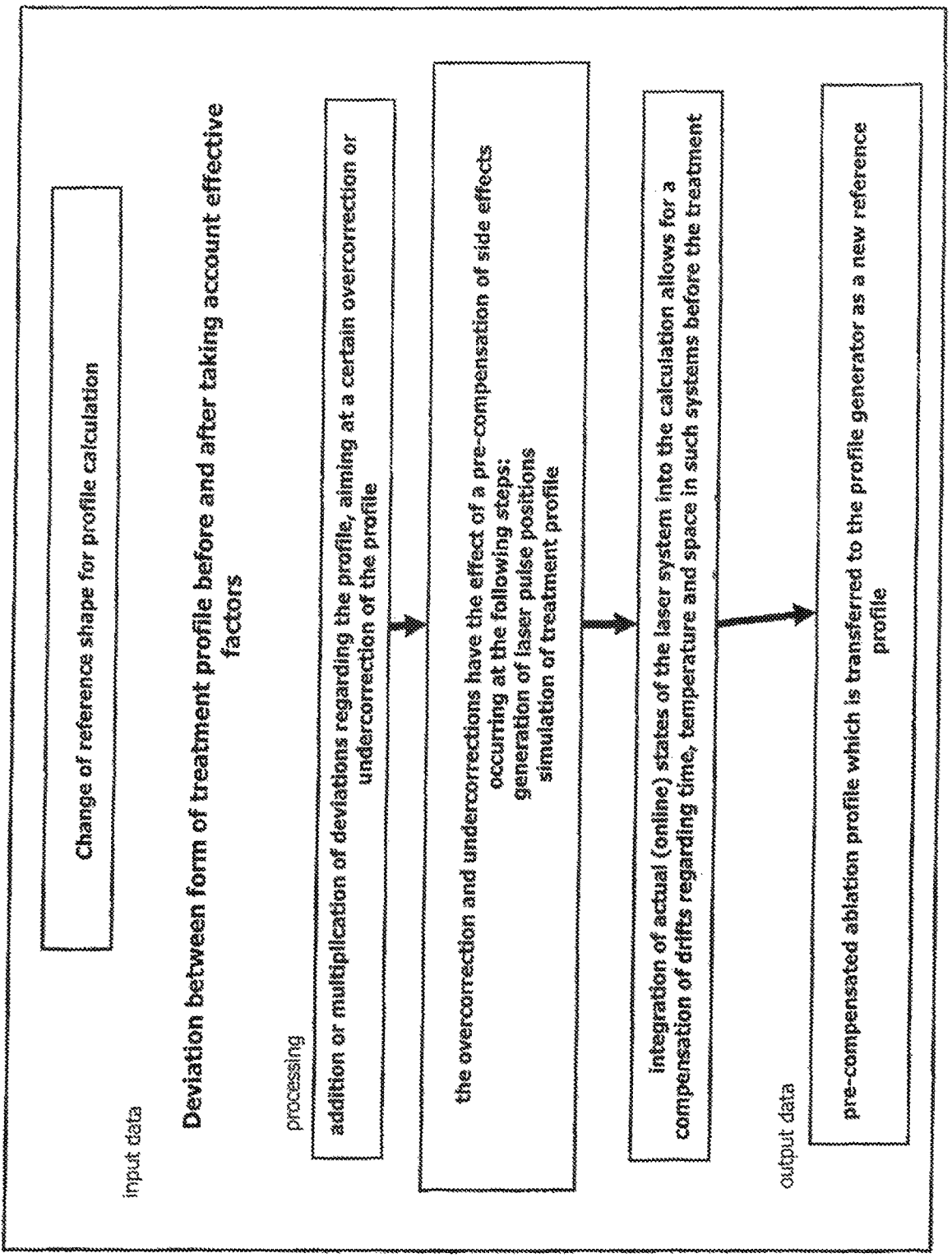

FIG. 6 shows a change of the reference form (of the cornea) for calculating an ablation profile. Under the headline "input data" the general purpose of the process is described. The purpose is to cope with the effect of varying input conditions on the result of the calculated treating profile.

Figure 7:
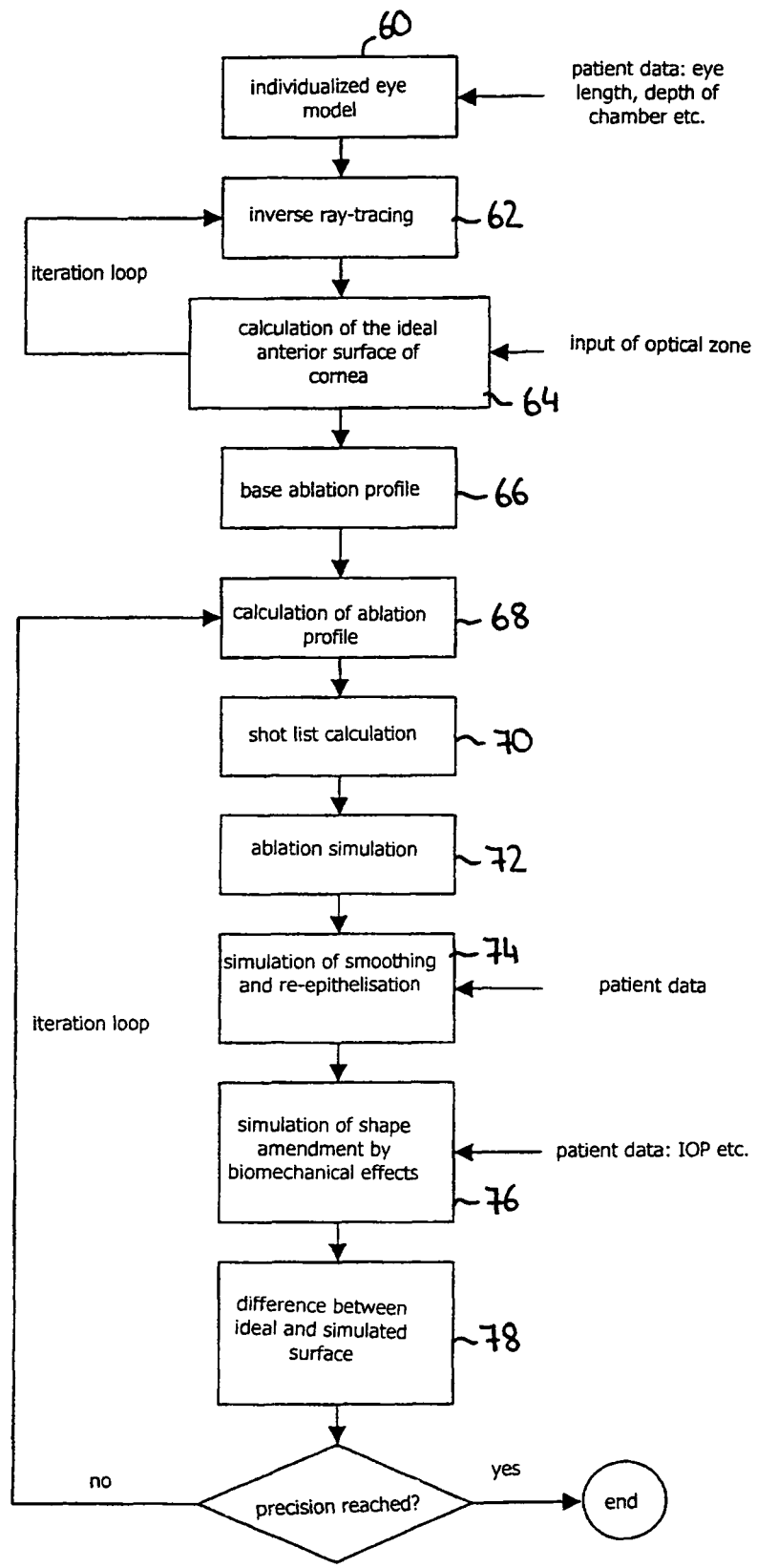
FIG. 7 a flow chart of a method for generating a control program for performing an ophthalmologic intervention at e.g. the cornea or an eye lens.

FIG. 7 shows an embodiment of the present invention using two iteration loops. The embodiment of the invention according to FIG. 7 provides for a first iteration loop for determining first an ideal cornea anterior surface to be achieved. In this embodiment, a second iteration loop, following the first iteration loop, corresponds essentially to the iteration loop described in connection with FIGS. 1 and 2. By the algorithm in accordance with FIG. 7 improvement is achieved regarding the precision of the correction, taking account of wavefront aberrations of higher order. This algorithm also allows treatment of irregularities of the cornea, like so-called central islands and also cicatrices. The data input interfaces used to input the above explained data into the program, are connected, with regard to the transfer of measuring data, to external measuring devices (e.g. topographer) directly. A design based on modules allows continued improvement, refinement and upgrading to cope with additional factors and conditions.

The algorithm according to FIG. 7 is explained in the following:

First, an individualized eye model (individualized with regard to the patient) is generated, as is explained above. In particular, the individual length of the patient's eye and, furthermore, the depth of the anterior chamber are used to generate the individual eye model. Thereafter, according to block 62, ray-tracing from the retina is performed in order to calculate and ideal anterior surface of the cornea to be achieved. This ray tracing from the retina of rays by using a model eye is based on the fact that the ideal image point of the optical system "eye" is known. It is the diffraction-limited focus at the retina. Based on this assumption, the ideal anterior surface of the cornea is derived, taking account of lens aberration and biometrical data, which results in said ideal focal point. This way, the ideal anterior surface of the cornea is obtained. The shown iteration loop is run until, based on the individualized eye model, the ideal anterior surface of the cornea is obtained on the basis of pregiven criteria (tolerances). Once the ideal anterior surface of the cornea is calculated, in block 74, optionally, optical zones can be input if, for example, the anterior surface of the cornea of the patient comprises two or more optical zones comprising different optical properties.

With the ideal anterior surface of the cornea, obtained this way, the initial profile (e.g. an ablation profile) is determined. That initial profile is called in FIG. 7 "basis ablation profile", see block 66. In other words, this embodiment is concerned with an ablation of the anterior surface of the cornea and the term "profile" refers to the ablation profile. In another (different) embodiment, the term "profile" may refer to another geometrical structure of change in the eye, e.g. the profile can refer to the geometry of a cut to be made by Fs-lasers within the cornea in order to generate a LASIK-flap. On the basis of said base profile the improved ablation profile is calculated, i.e. the difference between the given anterior surface of the cornea and the new anterior surface of the cornea to be achieved. The ablation profile is a certain shaped volume of corneal tissue to be removed.

Thereafter, in block 70, the list of laser pulses is generated, in particular the x, y, z-positions of the laser pulses are calculated.

Thereafter, in block 72, an ablation simulation is performed. The simulator simulates a theoretical result of the treatment on the basis of the afore-mentioned input data and conditions. At this point is, in addition to the above-described embodiments, a simulation of smoothing effects and a re-epithelisation possible. Such simulation is based on further patient data concerning empirical values regarding post-operative smoothing and healing. For example, depending on the individual patient, it can be assumed that with a young person, there is more rapid smoothing and healing as compared to an older person. Also there are dependencies from the sex and other individual differences. Such input is indicated at block 74.

Furthermore, according to block 76, there is a simulation of the change of shape by bio-mechanical effects, e.g. the above-discussed change of the cornea curvature due to intraocular pressure (IOP).

According to block 78, a difference is generated between the ideal and the simulated surface.

After block 78, a judgment is made. That judgment is based on the "difference between ideal and simulated surface". In other words, the judgment is a comparison between the simulated cornea shape with the reference cornea shape by applying certain tolerance criteria, i.e. allowed deviations from the reference cornea shape. Is the intended precision not achieved, the iteration loop is performed again on the basis of other data. Once the intended precision is achieved, the obtained control data are delivered to the laser control system in accordance with FIGS. 1 and 2.

In the following, further details of the above-described program modules are explained.

Figure 8:
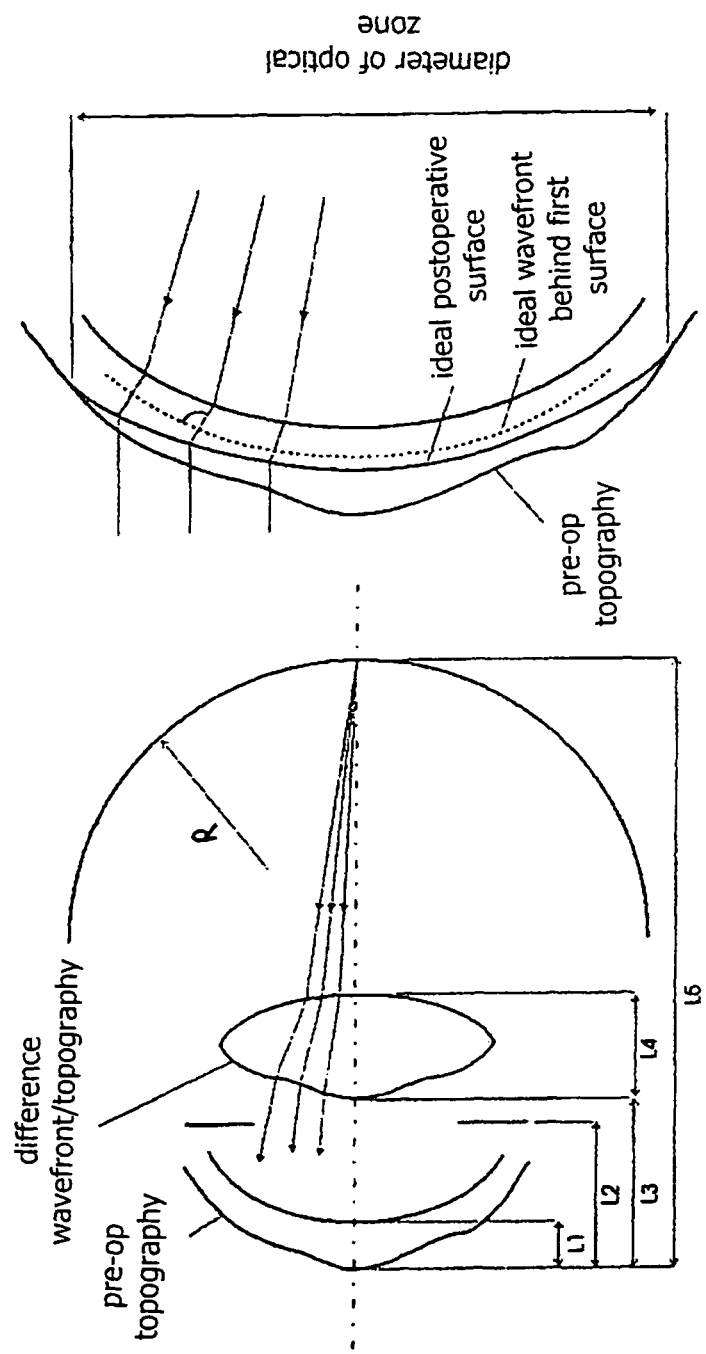
FIG. 8 schematically a determination of an individualized eye model and an ray-tracing from the retina for determining the ideal anterior surface of the cornea, FIG. 9 schematically the determination of a base ablation profile for an iteration.

With regard to the individualized eye model and the determination of the ideal anterior surface of the cornea for calculating the profile, the following applies:

FIG. 8 shows schematically the individualized eye model and an ray-tracing from the retina to determine the ideal anterior surface of the cornea. The following items are measured at the patient's eye (FIG. 8, left hand side): cornea topography, wavefront-aberration, image taken with a Scheimpflugcamera, thickness of cornea (L1), depth of anterior chamber (L2), position of lens (L3), thickness of lens (L4), length of eye (L5), curvature of retina (R).

When implementing such data to calculate the eye model, the steps are as follows:

modeling the basic lens form by measuring the thickness, or taking pictures with a Scheimpflugcamera;

calculating irregularities of the lens from the difference of the topography data and the wavefront aberration data;

making further assumptions regarding refractive indices of the media, form of the posterior surface of the cornea (constant of asphericity, central radius of curvature).

After determining the number of rays to be traced and the starting point (variant A) or the starting points (variant B) at the retina, the ray-tracing is started. It includes a sequential calculation of the refraction of the light at the anterior surface of the lens, at the posterior surface of the lens and at the anterior surface of the cornea in accordance with Snellius Law. Thereafter, the ideal anterior surface of the cornea is constructed. By so-called fitting of the derivation function to the normal-planes of the traced ray(s) after refraction at the posterior surface of the cornea, the un-known anterior surface of the cornea and the ideal wavefront can be determined with regard to the ideal focus point (variant A) or a focus area (variant B). This is illustrated in FIG. 8, right hand side, schematically. With variant B an averaging is performed with regard to the different angles of incidences of the optimized wavefronts. From the ideal wavefront, the ideal corneal surface can be derived.

This anterior surface of the cornea is then shifted axially until it touches the preoperative anterior surface of the cornea in the optical zone. The reconstruction of the ideal anterior surface it performed iteratively as the exact points of transition of the rays with regard to the new surface are not known and can only be obtained step-by-step.

Figure 9:
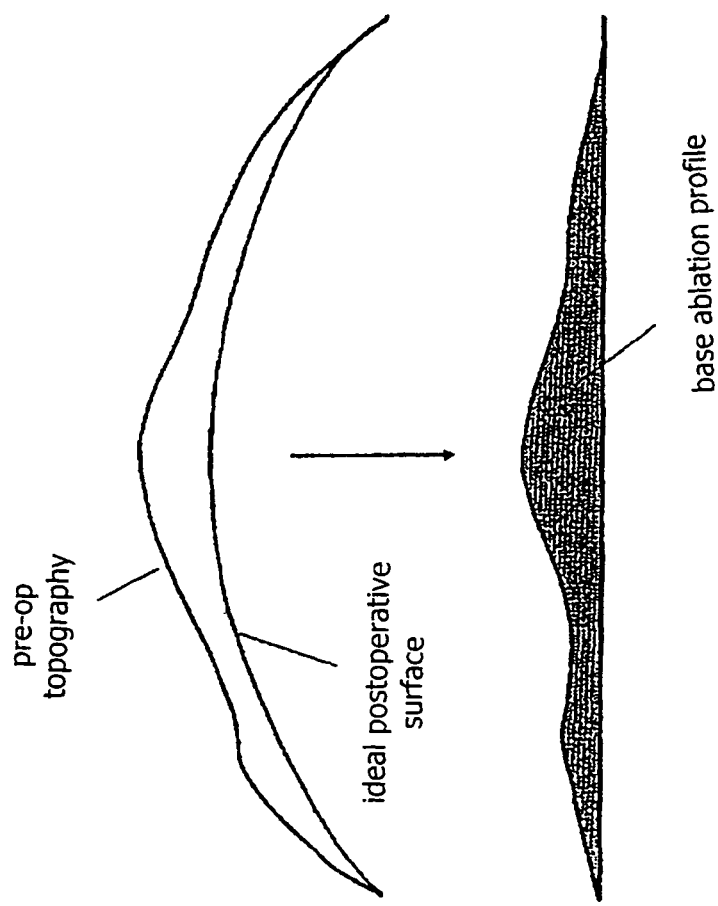

The profile used in connection with the above-captioned iterative process, which, when the invention is applied to LASIK, can be called the base ablation profile, is obtained in accordance with FIG. 9 which shows how the base ablation profile for the iterative process is obtained. It is the difference between the preoperatively measured cornea topography and the calculated ideal anterior surface of the cornea.

The base ablation profile serves as starting point of the iterative process in which the ablation profile is optimized under consideration of the diverse effective factors (see above). Different from an ablation profile calculated conventionally from wavefrontaberration, this base ablation profile contains already a compensation of the so-called multiple lens effect (as described by F. Manns et al.; Journal of Cateract and Refractive Surgery, 2002; 28:766-774). This effect is already taken care of when the ray tracing from the retina is performed.

As to the simulator:

The scanning spot ablation is simulated by calculation. The calculation is performed numerically. To this end both the topographic surface to be ablated as well as the raster of the spots are discretized at the same intervals. In order to take account of the above-stated different effects (for example the dependency of the ablation depth from the cornea curvature, reflection losses at the cornea due to different angles of incidence; different ablation effects because of the varying water content etc.), the ablation effect of each spot is determined for each individual laser pulse of the simulated treatment in dependence from the spot position (both afore-mentioned factors are dependent from the position in the x, y-plane) and the time (the water content is time dependent), and on the basis of the fluence of the laser radiation.

The simulation of the treatment can e.g. simulate treatment by an ablating laser (e.g. ArF-Laser) but also a change in the tissue itself can be simulated, caused by ultra-short highly focussed laser pulses (so-called plasmaablation or photodisruption). Furthermore, the simulation can be directed to optical properties (e.g. index of refraction) or material shift in artificial eye lenses (e.g. caused by capillary effects).

Figure 10:
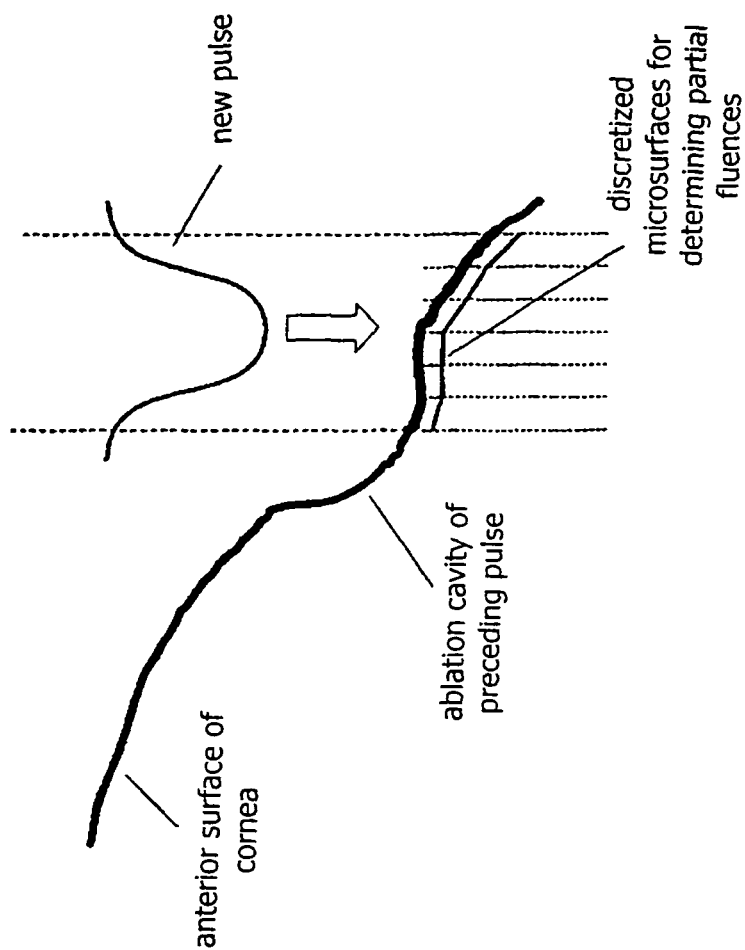
FIG. 10 schematical the adaptation of the fluence for each pulse with a changing cornea surface during simulation.

During such simulated ablation process or changing process, the anterior surface of the cornea and its local surface gradients change at each iteration loop. The effective fluences of the discretized laser pulses are calculated under consideration of the influential factors (for example dependency of the ablation depth from the cornea curvature and reflection losses at the cornea) separately, depending on the position of the laser shot. The effective fluences of the laser pulses are continuously calculated as a function of the varying surface. This is shown schematically in FIG. 10. FIG. 10 shows how the calculation of the fluence for each pulse is adapted to the changing cornea surface. FIG. 10 also shows the discretized microsurface areas, serving to calculate the fraction of the fluence effective in each discretized micro surface section, as shown in FIG. 10.

The simulation of the healing process and the smoothing process is performed essentially empirically and by applying the so-called Butterworth-Low-Pass-Filter of first order. These filters are applied to the surface to be ablated (see D. Huang et al. in Am. J. Ophtalmol.; 2003, 135 (3): 267-78).

If the simulation takes account of biomechanical changes of the cornea (e.g. due to the intraocular pressure), then a FE-model is generated (finite elements). The iteration process can then approximate the final cornea surface as a function of the local changes in cornea thickness. A constant internal pressure of the eye is assumed. The intraocular pressure of the eye of the patient is measured. Furthermore, other data specific to the patient can be observed, for example the individual strength of the tissue.

The simulation according to the present invention can also be summarized as a comparison of the calculated postoperative surface with the ideal surface in the judgment stage. According to this comparison, the initial ablation profile can be corrected. For example if the ablation obtained with the just finished iteration loop is too small, according to the judgment, in the next iteration loop the ablation is increased locally. The iteration is repeated until the target precision is obtained.

What is claimed is:

1. A method of controlling radiation in an ophthalmological treatment comprising:
   generating an eye model in three-dimensions and individualized for a patient subject to an ophthalmological treatment, wherein the eye model includes an initial corneal shape of a cornea of an eye of the patient, wherein the generating the eye model comprises:
      obtaining topography data of an eye lens of the eye of the patient by at least one of measuring a thickness of the eye lens or taking pictures with a Scheimpflugcamera;
      calculating irregularities of the eye lens from a difference of the topography data and wavefront aberration data; and
      assuming a form of the posterior surface of the cornea;
   determining a reference corneal shape by three-dimensional iterative ray-tracing from a retina using the eye model, wherein the reference corneal shape is optimized for post-treatment diffraction limited focus at the retina;
   determining a first difference between the reference corneal shape and the initial corneal shape to obtain a first ablation profile;
   generating control data for a plurality of laser pulses for controlling radiation in the ophthalmological treatment based on the first ablation profile, the control data including fluence data for the radiation and positioning data for sites of interaction between the radiation and the cornea;
   adjusting the control data to account for at least one of room temperature, humidity, water content of the cornea, the index of refraction of the eye, smoothing effects, re-epithelization, demographical data of the patient, intraocular pressure (TOP), and a minimum depth of sight for the postoperative eye;
   determining based on the positioning data whether to account for a reflection loss or a curvature of the cornea, and, when accounting for the reflection loss or the curvature, adjusting the fluence data;
   based on the eye model and the control data, calculating an interaction between the radiation and the cornea to obtain an estimated corneal shape, the calculating an interaction between the radiation and the cornea comprising:
      accounting for a fluence of each individual laser pulse of the plurality of laser pulses; and
      determining, based on the control data, an ablation effect for each individual laser pulse of the plurality of laser pulses;
   determining whether a resulting difference between the estimated corneal shape and the reference corneal shape is within a predetermined tolerance;
   controlling the radiation in the ophthalmological treatment using the control data when the resulting difference is within the predetermined tolerance; and when the resulting difference is not within the predetermined tolerance:
(a) based on the resulting difference, calculating an estimated ablation profile;
(b) updating control data based on the estimated ablation profile;
(c) based on the eye model and the updated control data, recalculating the interaction to update the estimated corneal shape;
(d) recalculating the resulting difference between the estimated corneal shape and the reference corneal shape;
(e) iteratively repeating steps (a) through (d) until the resulting difference is within a predetermined tolerance; and
(f) controlling the radiation in the ophthalmological treatment using the updated control data.

2. The method according to claim 1, wherein the reference corneal shape is an anterior corneal surface optimized with regard to a focus point at the retina of the eye model.

3. The method according to claim 1, wherein the reference cornea shape is an anterior corneal surface optimized with regard to a focus area at the retina of the eye model.

4. A method for controlling radiation in ophthalmological surgery to treat eye lenses comprising:
generating an eye model in three-dimensions and individualized for a patient subject to ophthalmological surgery on an eye lens of an eye, the eye model including an initial lens shape of the eye lens, wherein the generating an eye model comprises:
obtaining topography data of the eye lens by at least one of measuring a thickness of the eye lens or taking pictures with a Scheimpflugcamera;
calculating irregularities of the eye lens from a difference of the topography data and wavefront aberration data; and
assuming a form of the posterior surface of a cornea of the eye of the patient;
determining a reference lens shape by iterative three-dimensional ray tracing from a retina using the eye model, wherein the reference lens shape is optimized for post-surgical diffraction limited focus at the retina;
determining a first difference between the reference lens shape and the initial lens shape to obtain a first ablation profile;
generating control data for a plurality of laser pulses to control radiation for the ophthalmological surgery based on the first ablation profile, the control data including fluence data for the radiation and a position data describing sites of interaction between the radiation and the eye lens;
adjusting the control data to account for at least one of room temperature, humidity, water content of the eye, the index of refraction of the eye, smoothing effects, re-epithelization, demographical data of the patient, intraocular pressure (TOP), and a minimum depth of sight for the postoperative eye;
determining based on the positioning data whether to account for a reflection loss or a curvature of the cornea, and, when accounting for the reflection loss or the curvature, adjusting the fluence data;
based on the eye model and the control data, calculating an interaction between the radiation and the eye lens to obtain an estimated lens shape, the calculating an interaction between the radiation and the eye lens comprising:
accounting for a fluence of each individual laser pulse of the plurality of laser pulses; and
determining, based on the control data, an ablation effect for each individual laser pulse of the plurality of laser pulses;
determining whether a resulting difference between the estimated lens shape and the reference lens shape is within a predetermined tolerance;
controlling the radiation in the ophthalmological surgery to treat the eye lens using the control data when the resulting difference is within the predetermined tolerance; and
when the resulting difference is not within the predetermined tolerance:
(a) based on the resulting difference, calculating an estimated ablation profile;
(b) updating control data based on the estimated ablation profile;
(c) based on the eye model and the updated control data, recalculating the interaction to update the estimated lens shape;
(d) recalculating the resulting difference between the estimated lens shape and the reference lens shape;
(e) iteratively repeating steps (a) through (d) until the resulting difference is within a predetermined tolerance; and
(f) controlling the radiation in the ophthalmological surgery using the updated control data.

5. The method according to claim 4, wherein the reference lens shape is optimized for a focus point at the retina of the eye model.

6. The method according to claim 4, wherein the reference lens shape is optimized for a focus area at the retina of the eye model.

7. A method for controlling light acting upon artificial eye lenses in an ophthalmological treatment comprising:
generating an eye model in three-dimensions and individualized for a patient's eye subject to ophthalmological surgery, the eye model including an initial shape and a distribution of an index of refraction of an artificial eye lens, wherein the generating an eye model comprises:
obtaining topography data of the artificial eye lens form by at least one of measuring a thickness of the artificial eye lens or taking pictures with a Scheimpflugcamera;
calculating irregularities of the artificial eye lens from a difference of the topography data and wavefront aberration data; and
assuming a form of the posterior surface of a cornea of the eye of the patient;
determining a reference shape of the artificial eye lens by iterative three-dimensional ray tracing from a retina using the eye model, wherein the reference shape is optimized for post-surgical diffraction limited focus at the retina;
determining a first difference between the reference shape and the initial shape to obtain a first ablation profile;
generating control data for a plurality of laser pulses to control radiation based on the first ablation profile, the control data including fluence data for the radiation and positioning data for sites of interaction of the radiation and the artificial eye lens;
adjusting the control data to account for at least one of room temperature, humidity, water content of the eye, the index of refraction of the eye, smoothing effects, re-epithelization, demographical data of the patient, intraocular pressure (IOP), and a minimum depth of sight for the postoperative eye;

determining based on the positioning data whether to account for a reflection loss or a curvature of the cornea, and, when accounting for the reflection loss or the curvature, adjusting the fluence data;

based on the eye model and the control data, calculating an interaction between the radiation and the artificial eye lens to obtain an estimated shape of the artificial eye lens, the calculating an interaction between the radiation and the artificial eye lens comprising:

accounting for a fluence of each individual laser pulse of the plurality of laser pulses; and determining, based on the control data, an ablation effect for each individual laser pulse of the plurality of laser pulses;

determining whether a resulting difference between the estimated shape and the reference shape is within a predetermined tolerance;

controlling the radiation acting upon the artificial eye lens using the control data when the resulting difference is within the predetermined tolerance; and when the resulting difference is not within the predetermined tolerance:
(a) based on the resulting difference, calculating an estimated ablation profile;
(b) updating control data based on the estimated ablation profile;
(c) based on the eye model and the updated control data, recalculating the interaction to update the estimated shape of the artificial eye lens;
(d) recalculating the resulting difference between the estimated shape and the reference shape;
(e) iteratively repeating steps (a) through (d) until the resulting difference is within a predetermined tolerance; and
(f) controlling the radiation in the ophthalmological treatment using the updated control data.

8. The method according to claim 7, wherein the reference shape is optimized for a focus point at the retina of the eye model.

9. The method according to claim 7, wherein the reference shape is optimized for a focus area at the retina of the eye model.

10. Apparatus for controlling radiation in ophthalmological treatments, the apparatus comprising:
a radiation source;
a radiation beam shaping device;
a radiation beam scanner;
a processor having access to memory media, the memory media storing instructions which, when executed by the processor, cause the processor to:
generate an eye model in three-dimensions and individualized for a patient subject to an ophthalmological treatment, wherein the eye model includes an initial shape of a portion of an eye of the patient selected from at least one of a cornea of the eye and a lens of the eye, wherein the instructions to generate the eye model cause the processor to:
obtain topography data of the lens of the eye by at least one of measuring a thickness of the lens of the eye or taking pictures with a Scheimpflugcamera;
calculate irregularities of the lens of the eye from a difference of the topography data and wavefront aberration data; and
assume a form of the posterior surface of the cornea of the eye;

determine a reference shape of the portion of the eye by three-dimensional iterative ray-tracing from a retina using the eye model, wherein the reference shape is optimized for post-treatment diffraction limited focus at the retina;

determine a first difference between the reference shape and the initial shape to obtain a first ablation profile;

generate control data for a plurality of laser pulses for controlling radiation in the ophthalmological treatment based on the first ablation profile, the control data including fluence data for the radiation and positioning data for sites of interaction between the radiation and the portion of the eye;

adjust the control data to account for at least one of room temperature, humidity, water content of the cornea, the index of refraction of the eye, smoothing effects, re-epithelization, demographical data of the patient, intraocular pressure (TOP), and a minimum depth of sight for the postoperative eye;

determine based on the positioning data whether to account for a reflection loss or a curvature of the cornea of the eye, and, when accounting for the reflection loss or the curvature, adjust the fluence data;

based on the eye model and the control data, calculate an interaction between the radiation and the portion of the eye to obtain an estimated shape of the portion of the eye, wherein the instructions that cause the processor to calculate an interaction between the radiation and the portion of the eye comprise instructions to:
account for a fluence of each individual laser pulse of the plurality of laser pulses; and
determine, based on the control data, an ablation effect for each individual laser pulse of the plurality of laser pulses;

determine whether a resulting difference between the estimated shape and the reference shape is within a predetermined tolerance;

control the radiation in the ophthalmological treatment using the control data when the resulting difference is within the predetermined tolerance; and when the resulting difference is not within the predetermined tolerance:
(a) based on the resulting difference, calculating an estimated ablation profile;
(b) updating control data based on the estimated ablation profile;
(c) based on the eye model and the updated control data, recalculating the interaction to update the estimated shape of the portion of the eye;
(d) recalculating the resulting difference between the estimated shape and the reference shape;
(e) iteratively repeating steps (a) through (d) until the resulting difference is within a predetermined tolerance; and
(f) controlling the radiation in the ophthalmological treatment using the updated control data.

11. The apparatus of claim 10, wherein the reference shape is optimized for a focus point at the retina of the eye model.

12. The apparatus of claim 10, wherein the reference shape is optimized for a focus area at the retina of the eye model.

13. Apparatus for controlling light acting upon artificial eye lenses, the apparatus comprising:
a radiation source;

a radiation beam shaping device;
a radiation beam scanner;
a processor having access to memory media, the memory media storing instructions which, when executed by the processor, cause the processor to:
  generate an eye model in three-dimensions and individualized for a patient's eye subject to ophthalmological surgery, the eye model including an initial shape and a distribution of an index of refraction of an artificial eye lens, wherein the instructions to generate an eye model cause the processor to:
    obtain topography data of the artificial eye lens by at least one of measuring a thickness of the artificial eye lens of the patient or taking pictures with a Scheimpflugcamera;
    calculate irregularities of the lens from a difference of the topography data and wavefront aberration data; and
    assume a form of the posterior surface of a cornea of the eye of the patient;
  determine a reference shape of the artificial eye lens by iterative three-dimensional ray tracing from a retina using the eye model, wherein the reference shape is optimized for post-surgical diffraction limited focus at the retina;
  determine a first difference between the reference shape and the initial shape to obtain a first ablation profile;
  generate control data for a plurality of laser pulses to control radiation based on the first ablation profile, the control data including fluence data for the radiation and positioning data for sites of interaction of the radiation and the artificial eye lens;
  adjust the control data to account for at least one of room temperature, humidity, water content of the cornea, the index of refraction of the artificial eye lens, smoothing effects, re-epithelization, demographical data of the patient, intraocular pressure (TOP), and a minimum depth of sight for the post-operative eye;
  determine based on the positioning data whether to account for a reflection loss or a curvature of the cornea, and, when accounting for the reflection loss or the curvature, adjust the fluence data;
  based on the eye model and the control data, calculate an interaction between the radiation and the artificial eye lens to obtain an estimated shape of the artificial eye lens, wherein the instructions that cause the processor to calculate an interaction between the radiation artificial eye lens comprise instructions to:
    account for a fluence of each individual laser pulse of the plurality of laser pulses; and
    determine, based on the control data, an ablation effect for each individual laser pulse of the plurality of laser pulses;
  determine whether a resulting difference between the estimated shape and the reference shape is within predetermined tolerance;
  control the radiation acting upon the artificial eye lens using the control data when the resulting difference is within the predetermined tolerance; and
  when the resulting difference is not within the predetermined tolerance:
    (a) based on the resulting difference, calculating an estimated ablation profile;
    (b) updating control data based on the estimated ablation profile;
    (c) based on the eye model and the updated control data, recalculating the interaction to update the estimated shape of the artificial eye lens;
    (d) recalculating the resulting difference between the estimated shape and the reference shape;
    (e) iteratively repeating steps (a) through (d) until the resulting difference is within a predetermined tolerance; and
    (f) controlling the radiation in the ophthalmological treatment using the updated control data.

14. The apparatus of claim 13, wherein the reference shape is optimized for a focus point at the retina of the eye model.

15. The apparatus of claim 13, wherein the reference shape is optimized for a focus area at the retina of the eye model.

* * * * *